(12) United States Patent
Andree et al.

(10) Patent No.: US 6,277,789 B1
(45) Date of Patent: Aug. 21, 2001

(54) SUBSTITUTED PHENYLURACILS

(76) Inventors: Roland Andree; Otto Schallner; Katharina Voigt, all of c/o Bayer Aktiengesellschaft, D 51368 Leverkusen (DE); Markus Dollinger, 13210 Knox, Overland Park, KS (US) 66213; Hans-Joachim Santel, Grünstrasse 9a, D 51371 Leverkusen (DE)

(*) Notice: Subject to any disclaimer, the term of this patent is extended or adjusted under 35 U.S.C. 154(b) by 0 days.

(21) Appl. No.: 09/486,916

(22) PCT Filed: Sep. 7, 1998

(86) PCT No.: PCT/EP98/05659
§ 371 Date: Mar. 1, 2000
§ 102(e) Date: Mar. 1, 2000

(87) PCT Pub. No.: WO99/12913
PCT Pub. Date: Mar. 18, 1999

(30) Foreign Application Priority Data

Sep. 10, 1997 (DE) .............................................. 197 39 638

(51) Int. Cl.[7] .................... C07D 239/54; C07D 239/553; A01N 43/54
(52) U.S. Cl. .......................... 504/243; 544/296; 544/309; 544/310; 544/311; 544/312; 544/313; 544/314

(58) Field of Search .............................. 504/243; 544/309, 544/310, 311, 312, 313, 314, 296

(56) References Cited

FOREIGN PATENT DOCUMENTS

WO97/08953    3/1997   (WO).

*Primary Examiner*—John M. Ford
(74) *Attorney, Agent, or Firm*—Joseph C. Gil; Jackie Ann Zurcher

(57) ABSTRACT

The invention relates to substituted phenyluracils of the general formula (I)

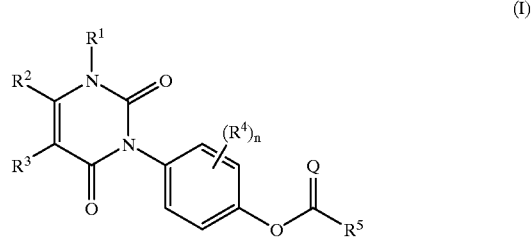

in which the radicals $R^1$ to $R^5$, Q and n are each as defined in the description, and to processes for their preparation and to their use as herbicides.

10 Claims, No Drawings

SUBSTITUTED PHENYLURACILS

This is a 371 of PCT/EP98/05659, filed Sep. 7, 1998.

1. Technical Field of the Invention

The invention relates to novel substituted phenyluracils, to processes for their preparation and to their use as herbicides.

2. Background of the Invention

A large number of substituted aryluracils is already known from the (patent) literature (cf. JP-A-04178373-cited in Chem. Abstracts 118:59721; JP-A-05039272-cited in Chem. Abstracts 119:180805; JP-A-05202031-cited in Chem. Abstracts 120:107048; EP-A-545206; U.S. Pat. No. 5,169,430; U.S. Pat. No. 5,344,812; U.S. Pat. No. 5,399,543; WO-A-95/17096; WO-A-97/08953). However, these compounds have hitherto not attained any particular importance.

DETAILED DESCRIPTION OF THE INVENTION

Novel substituted phenyluracils of the general formula (I)

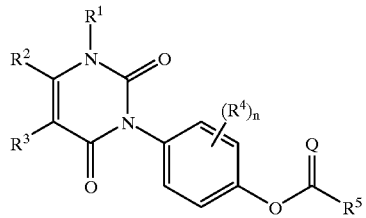

(I)

in which n represents the numbers 0, 1, 2 or 3,

Q represents oxygen or sulphur, $R^1$ represents hydrogen, amino or optionally substituted alkyl, $R^2$ represents carboxyl, cyano, carbamoyl, thiocarbamoyl or represents in each case optionally substituted alkyl or alkoxycarbonyl, $R^3$ represents hydrogen, halogen or optionally substituted alkyl, $R^4$ represents nitro, amino, hydroxyl, carboxyl, cyano, carbarnoyl, thiocarbamoyl, sulpho, chlorosulphonyl, ainiosulphonyl, halogen, or represents in each case optionally substituted alkyl, alkoxy, alkylthio, alkylsulphinyl, alkylsulphonyl, alkylamino, alkylcarbonyl, alkoxycarbonyl, alkylaminocarbonyl, alkylcarbonylamino, alkoxycarbonylamino, alkylsulphonylamino, bis-alkylcarbonyl-amino, bis-alkylsulphonyl-amino or N-alkylcarbonyl-N-alkylsulphonyl-amino, and $R^5$ represents hydrogen or represents in each case optionally substituted alkyl, alkoxy, alkylthio, alkylamino, dialkylamino, alkenyl, alkenyloxy, alkenylamino, alkinyl, alkinyloxy, alkinylainio, cycloalkyl, cycloalkyloxy, cycloalkylamino, cycloalkylalkyl, cycloalkylalkoxy, cycloalkylalkylamino, aryl, aryloxy, arylthio, arylamino, arylalkyl, arylalkyoxy, arylalkylthio, arylalkylamino, heterocyclyl or heterocyclylalkyl have now been found.

The invention preferably provides compounds of the formula (I) in which n represents the numbers 0, 1, 2 or 3, Q represents oxygen or sulphur, $R^1$ represents hydrogen, represents amino or represents optionally cyano-, fluorine-, or chlorine-substituted alkyl having 1 to 4 carbon atoms, $R^2$ represents cyano, carboxyl, carbamoyl, thiocarbamoyl or represents in each case optionally cyano-, fluorine- or chlorine-substituted alkyl or alkoxycarbonyl having in each case up to 4 carbon atoms, $R^3$ represents hydrogen, fluorine, chlorine, bromine or alkyl having 1 to 4 carbon atoms, $R^4$ represents nitro, amino, hydroxyl, carboxyl, cyano, carbamoyl, thiocarbamoyl, sulfo, chlorosulphonyl, aminosulphonyl, halogen, or represents in each case optionally cyano-, halogen- or $C_1$–$C_4$-alkoxy-substituted alkyl, alkoxy, alkylthio, alkylsulphinyl, alkylsulphonyl, alkylamino, alkylcarbonyl, alkoxycarbonyl, alkylaminocarbonyl, alkylcarbonylaminno, alkoxycarbonylamino, alkylsulphonylamino, bis-alkylcarbonyl-amino, bis-alkylsulphonyl-amino or N-alkylcarbonyl-N-alkylsulphonyl-amino having in each case up to 5 carbon atoms in the alkyl groups, and $R^5$ represents hydrogen, represents in each case optionally cyano-, halogen- or $C_1$–$C_4$-alkoxy-substituted alkyl, alkoxy, alkylthio, alkylamino or dialkylamino having in each case 1 to 5 carbon atoms, represents in each case optionally cyano- or halogen-substituted alkenyl, alkenyloxy, alkenylamino, alkinyl, alkinyloxy or alkinylamino having in each case up to 5 carbon atoms, represents in each case optionally cyano-, halogen- or $C_1$–$C_4$-alkyl-substituted cycloalkyl, cycloalkyloxy, cycloalkylamino, cycloalkylalkyl, cycloalkylalkoxy or cycloalkylalkylamino having in each case 3 to 6 carbon atomns in the cycloalkyl groups and optionally 1 to 3 carbon atomns in the alkyl moieties, represents in each case optionally nitro-, cyano-, halogen-, $C_1$–$C_4$-alkyl-, $C_1$–$C_4$-halogenoalkyl-, $C_1$–$C_4$-alkoxy-, $C_1$–$C_4$-halogenoalkoxy-, $C_1$–$C_4$-alkylthio-, $C_1$–$C_4$-halogenoalkylthio-, $C_1$–$C_4$-alkylsulphinyl-, $C_1$–$C_4$-halogenoalkylsulphinyl-, $C_1$–$C_4$-alkylsulphonyl-, $C_1$–$C_4$-halogenoalkylsulphonyl- or phenyl-substituted aryl, aryloxy, arylthio, arylamino, arylalkyl, arylalkoxy, arylalkylthio or arylalkylamino having in each case 6 or 10 carbon atoms in the aryl groups and optionally 1 to 3 carbon atoms in the alkyl moieties, or represents in each case optionally cyano-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted heterocyclyl or heterocyclylalkyl from the group consisting of furyl, tetrahydrofuryl, furyl-$C_1$–$C_4$-alkyl, benzofuryl, benzofuryl-$C_1$–$C_4$-alkyl, thienyl, thienyl-$C_1$–$C_4$-alkyl, benzothienyl, benzothienyl-$C_1$–$C_4$-alkyl, oxazolyl, oxazolyl-$C_1$–$C_4$-alkyl, benzoxazolyl, benzoxazolyl-$C_1$–$C_4$-alkyl, isoxazolyl, isoxazolyl-$C_1$–$C_4$-alkyl, benzisoxazolyl, benzisoxazolyl-$C_1$–$C_4$-alkyl, thiazolyl, thiazolyl-$C_1$–$C_4$-alkyl, benzothiazolyl, benzothiazolyl-$C_1$–$C_4$-alkyl, pyrazolyl, pyrazolyl-$C_1$–$C_4$-alkyl, oxadiazolyl, oxadiazolyl-$C_1$–$C_4$-alkyl, thiadiazolyl, thiadiazolyl-$C_1$–$C_4$-alkyl, pyridyl, pyridyl-$C_1$–$C_4$-alkyl, quinolyl, quinolyl-$C_1$–$C_4$-alkyl, pyrimiyl, pyrimidyl-$C_1$–$C_4$-alkyl.

The invention relates in particular to compounds of the formula (I) in which n represents the numbers 0, 1 or 2, Q represents oxygen or sulphur, $R^1$ represents hydrogen, amino, methyl or ethyl, $R^2$ represents cyano, carboxyl, carbamoyl, thiocarbamoyl, methyl, ethyl, fluoromethyl, chloromethyl, difluoromethyl, dichloromethyl, trifluoromethyl, trichloromethyl, chlorodifluoromethyl, fluorodichloromethyl, fluoroethyl, chioroethyl, difluoroethyl, dichloroethyl, chlorofluoroethyl, trifluoroethyl, trichloroethyl, chlorodifluoroethyl, fluorodichloroethyl, pentafluoroethyl, methoxycarbonyl or ethoxycarbonyl, $R^3$ represents hydrogen, chlorine, bromine or methyl, $R^4$ represents nitro, amino, hydroxyl, carboxyl, cyano, carbamoyl, thiocarbamoyl, sulpho, chlorosulphonyl, aminosulphonyl, fluorine, chlorine, bromine, or represents in each case optionally cyano-, fluorine-, chlorine-, bromine-, methoxy- or ethoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, methylsulphonyl, ethylsulphonyl, methylamino, ethylamino, n- or i-propylamino, n-, i-, s- or t-butylamino, acetyl, propionyl, n- or i-butyroyl, methoxycarbonyl, ethoxycarbonyl, n- or i-propoxycarbonyl, methylaminocarbonyl, ethylaminocarbonyl, acetylamino, propionylamino, n- or i-butyroylamino, methoxycarbonylamino, ethoxycarbonylamino, methylsulphonylamino, ethylsulphonylamino, n- or i-propylsulphonylamino, n-, i-, s- or t-butylsulphonylamino, bis-methylsulphonyl-amino, bis-ethylsulphonyl-amino, N-acetyl-N-methylsulphonyl-amino or N-acetyl-N-ethylsulphonyl-amino, and $R^5$ represents hydrogen, represents in each case optionally cyano-, fluorine-, chlorine-, methoxy-, ethoxy-, n- or i-propoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino, represents in each case optionally cyano-, fluorine-, chlorine- or bromine-substituted ethenyl, propenyl, butenyl, propenyloxy, butenyloxy, propenylamino, butenylamino, ethinyl, propinyl, butinyl, propinyloxy, butinyloxy, propinylamino or butinylamino, represents in each case optionally cyano-, fluorine-, chlorine-, methyl- or ethyl-substituted cyclopropyl, cyclobutyl, cyclopentyl, cyclohexyl, cyclopropyloxy, cyclobutyloxy, cyclopentyloxy, cyclohexyloxy, cyclopropylamino, cyclobutylamino, cyclo-pentylamino, cyclohexylamino, cyclopropylmethyl, cyclobutylmethyl, cyclopentylmethyl, cyclohexylmethyl, cyclopropylmethoxy, cyclobutylmethoxy, cyclopentylmethoxy, cyclopropylmethylamino, cyclobutylmethylamino, cyclopentylmethylamino or cyclohexylmethylamino, represents in each case optionally nitro-, cyano-, fluorine-, chlorine-, bromiane-, methyl-, ethyl-, n- or i-propyl-, n-, i-, s- or t-butyl-, trifluoromethyl-, methoxy-, ethoxy-, n- or i-propoxy-, difluoromethoxy-, trifluoromethoxy-, methylthio-, ethylthio-, difluoromethylthio-, trifluoromethylthio-, methylsulphinyl-, ethylsulphinyl-, trifluoromethylsulphinyl-, methylsulphonyl-, ethylsulphonyl-, trifluoromethylsulphonyl- or phenyl-substituted phenyl, phenoxy, phenylthio, phenylamino, benzyl, benzyloxy, benzylthio or benzylamino, or represents in each case optionally cyano-, fluorine-, chlorine-, brormine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted heterocyclyl or heterocyclylalkyl from the group consisting of furyl, tetrahydroluryl, furylmethyl, benzofuryl, benzofurylmethyl, thienyl, thienylmethyl, benzothienyl, benzothienylmethyl, oxazolyl, oxazolylmethyl, benzoxazolyl, benzoxazolylmethyl, isoxazolyl, isoxazolylmethyl, benzisoxazolyl, benzoxazolylmethyl, thiazoyl, thiazolylmethyl, benzothiazolyl, benzothiazolylmethyl, pyrazolyl, pyrazolylmethyl, oxadiazolyl, oxadiazolylmethyl, thiadiazolyl, thiadiazolylmethyl, pyridyl, pyridylmethyl, quinolyl, quinolylmethyl, pyrimidyl, pyrimidylmethyl.

In the definitions, the saturated or unsaturated hydrocarbon chains, such as alkyl, alkenyl or alkinyl, are in each case straight-chain or branched.

Halogen generally represents fluorine, chlorine, bromine or iodine, preferably represents fluorine, chlorine or bromine, in particular represents fluorine or chlorine.

The abovementioned general or preferred radical definitions apply both to the end products of the formula (I) and, correspondingly, to the starting materials or intermediates required in each case for the preparation. These radical definitions can be combined with one another at will, i.e. including combinations between the given preferred ranges.

The novel substituted phenyluracils of the general formula (I) have strong and selective herbicidal activity.

The novel substituted phenyluracils of the general formula (I) are obtained when hydroxyphenyluracils of the general formula (II)

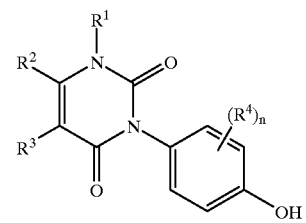

(II)

in which n, $R^1$, $R^2$, $R^3$ and $R^4$ are as defined above are reacted with acylating agents of the general formula (III)

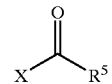

(III)

in which $R^5$ is as defined above and

X represents halogen or the grouping —O—CO—$R^5$, or, in the case that $R^5$ in the formula (I) represents atkylamino, alkenylamino, alkinylamino, cycloalkylamino, cycloalkylalkylamino, arylamino or arylalkylamino, with corresponding iso(thio)cyanates of the general formula (IV)

$$Q=C=N—R^6 \qquad (IV)$$

in which
Q is as defined above and
$R^6$ represents in each case optionally substituted alkyl, alkenyl, alkinyl, cycloalkyl, cycloalkylalkyl, aryl or arylalkyl,
if appropriate in the presence of a diluent and if appropriate in the presence of a reaction auxiliary and, if appropriate, subsequent reactions within the scope of the definition of the substituents are carried out by customary methods.

In this context, subsequent reactions are to be understood as being essentially substitution reactions in which compounds of the general formula (I) in which $R^1$ represents hydrogen are converted by amination reactions, for example with 1-aminooxy-2,4-dinitrobenzene, into corresponding aminouracils, or converted by alkylation reactions into corresponding alkyluracils (cf. the Preparation Examples).

Using, for example, 3-(3-fluoro-4-hydroxy-phenyl)-1-methyl-6-trifluoromethyl-(1H,3H)-pyrimidine-2,4-dione and 3,4-dichloro-benzoyl chloride as starting materials, the course of the reaction in the process according to the invention can be illustrated by the following formula scheme:

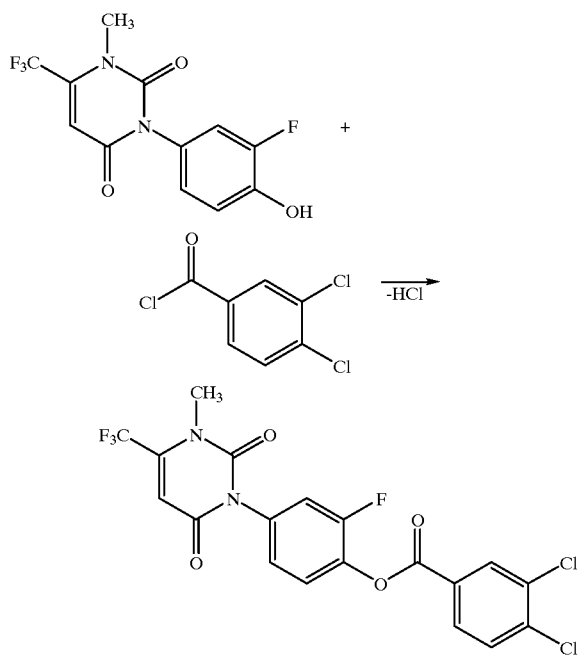

The formula (II) provides a general definition of the hydroxyphenyluracils to be used as starting materials in the process according to the invention for preparing compounds of the formula (I). In the formula (II), n, $R^1$, $R^2$, $R^3$ and $R^4$ preferably or in particular have those meanings which have already been mentioned above in connection with the description of the compounds of the formula (I) according to the invention as being preferred or as being particularly preferred for n, $R^1$, $R^2$, $R^3$ and $R^4$.

The starting materials of the general formula (II) are known and/or can be prepared by processes known per se (cf. EP-A-545206, JP-A-04178373).

The aminouracils of the general formula (IIa)

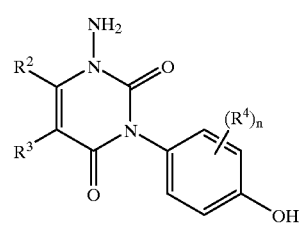

(IIa)

in which
n, $R^2$, $R^3$ and $R^4$ are as defined above
are not yet known from the literature and, as novel substances, form part of the subject-matter of the present invention.

The novel arnnouracils of the general formula (IIa) are obtained when uracils of the general formula (IIb)

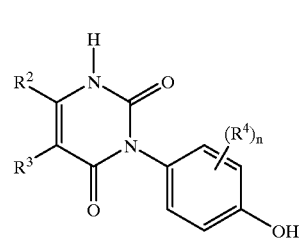

(IIb)

in which
n, $R^2$, $R^3$ and $R^4$ are as defined above
are reacted with an electrophilic arinating agent, such as, for example, 1-aminooxy-2,3-dinitro-benzene, if appropriate in the presence of a reaction auxiliary, such as, for example, sodium bicarbonate, and if appropriate in the presence of a diluent, such as, for example, N,N-dimethyl-formamide, at temperatures between 0° C. and 100° C.

The formula (III) provides a general definition of the acylating agents further to be used as starting materials in the process according to the invention. In the formula (III), Q and $R^5$ preferably or in particular have those meanings which have already been mentioned above in connection with the description of the compounds of the formula (I) according to the invention as being preferred or as being particularly preferred for Q and $R^5$; X preferably represents fluorine, chlorine, bromine or the grouping —O—CQ—$R^5$; in particular represents chlorine or the grouping —O—CQ—$R^5$, where Q and $R^5$ have the meanings mentioned above as being preferred or as being particularly preferred.

The starting materials of the general formula (III) are known organic chemicals for synthesis.

The formula (IV) provides a general definition of the iso(thio)cyanates further to be used if appropriate as starting materials in the process according to the invention. In the formula (IV), Q preferably or in particular has that meaning which has already been mentioned above in connection with the description of the compounds of the formula (I) according to the invention as being preferred or as being particularly preferred for Q; $R^6$ preferably represents optionally cyano-, halogen- or $C_1$–$C_4$-alkoxy-substituted alkylamino having 1 to 5 carbon atoms, represents in each case optionally cyano- or halogen-substituted alkenylamino or aikinylamino having in each case up to 5 carbon atoms, represents in each case optionally cyano-, halogen- or $C_1$–$C_4$-alkyl-substituted cycloalkylamino or cycloalkylalkylamino having 3 to 6 carbon atoms in the cycloalkyl groups and optionally 1 to 3 carbon atoms in the alkyl moiety, or represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy, difluoromethoxy-, trifluoromethoxy-, methylthio-, ethylthio-, difluoromethylthio-, trifluoromethylthio-, methylsulphinyl-, ethylsulphinyl-, trifluoromethylsulphinyl-, methylsulphonyl-, ethylsulphonyl- or trifluoromethylsulphonyl-substituted arylamino or arylalkylamino having in each case 6 or 10 carbon atoms in the aryl groups and optionally 1 to 3 carbon atoms in the alkyl moiety.

The starting materials of the general formula (IV) are known organic chemicals for synthesis.

The process according to the invention for preparing the compounds of the general formula (I) is optionally carried out using a diluent. Suitable diluents for carrying out the process according to the invention are, especially, inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketones; nitriles, such as acetonitrile, propionitrile or butyronitrile; amides, such as N,N-dimethylformamide, N,N-dimethylacetamide, N-methyl-formanilide, N-methyl-pyrrolidone or hexamethylphosphoric triamide; esters such as methyl acetate or ethyl acetate, sulphoxides, such as dimethyl sulphoxide. If carboxylic anhydrides which are liquid under the reaction conditions, such as, for example, acetic anhydride, are employed as starting materials, it is also possible to use them simultaneously in excess as diluent.

The process according to the invention for preparing the compounds of the general formula (I) is optionally carried out using a reaction auxiliary. Suitable reaction auxiliaries for the process according to the invention are, in general, the customary inorganic or organic bases or acid acceptors. These preferably include alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide, n-, i-, s- or t-butoxide or potassium methoxide, ethoxide, n- or i-propoxide, n-, i-, s- or t-butoxide; furthermore also basic organic nitrogen compounds, such as, for example, trimethylamine, triethylamine, tripropylamine, tributylamine, ethyl-diisopropylamnine, N,N-dimethyl-cyclohexylamine, dicyclohexylamine, ethyl-dicyclohexylamine, N,N-dimethyl-aniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 4-dimethylamino-pyridine, N-methyl-piperidine, 1,4-diazabicyclo[2,2,2]-octane (DABCO), 1,5-diazabicyclo[4,3,0]-non-5-ene (DBN), or 8-diazabicyclo[5,4,0]-undec-7-ene (DBU).

When carrying out the process according to the invention, the reaction temperatures can be varied within a relatively wide range. In general, the process is carried out at temperatures between 0° C. and 200° C., preferably between 20° C. and 150° C. The process according to the invention is generally carried out under atmospheric pressure. However, it is also possible to carry out the process according to the invention under elevated or reduced pressure—generally between 0.1 bar and 10 bar.

For carrying out the process according to the invention, the starting materials are generally employed in approximately equimolar amounts. However, it is also possible for one of the components to be used in a relatively large excess. The reaction is generally carried out in a suitable diluent, if appropriate in the presence of a reaction auxiliary, and the reaction mixture is generally stirred at the required temperature for several hours. Work-up is carried out by customary methods (cf. the Preparation Examples).

The active compounds according to the invention can be used as defoliants, desiccants, haulm killers and, especially, as weed killers. By weeds in the broadest sense there are to be understood all plants which grow in locations where they are undesired. Whether the substances according to the invention act as total or selective herbicides depends essentially on the amount used.

The active compounds according to the invention can be used, for example, in connection with the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus, Taraxacum.

Dicotyledonous crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis, Cucurbita.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus, Apera.

Monocotyledonous crops of the genera: Oryza, Zea, Triticum, Hordeum, Avena, Secale, Sorghum, Panicum, Saccharum, Ananas, Asparagus, Allium.

However, the use of the active compounds according to the invention is in no way restricted to these genera, but also extends in the same manner to other plants.

Depending on the concentration, the compounds are suitable for total weed control, for example on industrial terrain and rail tracks and on paths and areas with or without tree growth. Equally, the compounds can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantings and hop fields, on lawns and turf and pastures and for selective weed control in annual crops.

The compounds of the formula (I) according to the invention are particularly suitable for selective control of monocotyledonous and dicotyledonous weeds in monocotyledonous and dicotyledonous crops, both by the pre-emergence and by the post-emergence method.

The active compounds can be converted into the customary formulations, such as solutions, emulsions, wettable powders, suspensions, powders, dusts, pastes, soluble powders, granules, suspo-emulsion concentrates, natural and synthetic substances impregnated with active compound, and microencapsulations in polymeric substances.

These formulations are produced in a known manner, for example by mixing the active compounds with extenders, that is to say liquid solvents and/or solid carriers, optionally with the use of surfactants, that is to say emulsifiers and/or dispersants and/or foam formers.

If the extender used is water, it is also possible to use, for example, organic solvents as auxiliary solvents. Liquid solvents which are mainly suitable are: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulphoxide, and water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks, such as calcite, marble, pumice, sepiolite, dolomite and synthetic granules of inorganic and organic meals, and granules of organic material, such as sawdust, coconut shells, maize cobs and tobacco stalks; suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignosulphite waste liquors and methylcellulose.

Tackifiers, such as carboxymethylcellulose, natural and synthetic polymers in the form of powders, granules or latices, such as gum arabic, polyvinyl alcohol and polyvinyl acetate, and also natural phospholipids, such as cephalins and lecithins, and synthetic phospholipids can be used in the formulations. Other possible additives are mineral and vegetable oils.

It is possible to use dyestuffs, such as inorganic pigments, for example iron oxide, titanium oxide, Prussian blue, and organic dyestuffs, such as alizarin dyestuffs, azo dyestuffs and metal phthalocyanine dyestuffs, and trace nutrients, such as salts of iron, manganese, boron, copper, cobalt, molybdenum and zinc.

The formulations generally comprise between 0.1 and 95 per cent by weight of active compound, preferably between 0.5 and 90%.

For controlling weeds, the active compounds according to the invention, as such or in the form of their formulations, can also be used as mixtures with known herbicides, finished formulations or tank mixes being possible.

Possible components for the mixtures are known herbicides, for example acetochlor, acifluorfen(-sodium), aclonifen, alachlor, alloxydim(-sodium), ametryne, amidochlor, amidosulfuron, anilofos, asulam, atrazine, azafenidin, azimsulfuron, benazolin(-ethyl), benfuresate, bensulfuron(-methyl), bentazone, benzofenap, benzoylprop (-ethyl), bialaphos, bifenox, bispyribac(-sodium), bromobutide, bromofenoxim, bromoxynil, butachlor, butroxydim, butylate, cafenstrole, caloxydim, carbetamide, carfentrazone(-ethyl), chlomethoxyfen, chloramben, chloridazon, chlorimuron(-ethyl), chlornitrofen, chlorsulfuron, chlorotoluron, cinmethylin, cinosulfuron, clethodim, clodinafop(-propargyl), clomazone, clomeprop, clopyralid, clopyrasulfuron(-methyl), cloransulam(-methyl), cumyluron, cyanazine, cycloate, cyclosulfamuron, cycloxydim, cyhalofop(-butyl), 2,4-D, 2,4-DB, 2,4-DP, desmedipham, diallate, dicamba, diclofop(-methyl), diclosulam, diethatyl(-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epoprodan, EPTC, esprocarb, ethalfluralin, ethametsulfuron(-methyl), ethofumesate, ethoxyfen, ethoxysutfuron, etobenzanid, fenoxaprop-(-P-ethyl), flamprop(-isopropyl), flamprop(-isopropyl-L), flamprop(-methyl), flazasulfuron, fluazifop(-P-butyl), flumetsulam, flumiclorac(-pentyl), flumioxazin, flumipropyn, flumetsulam, fluometuron, fluorochloridone, fluoroglycofen(-ethyl), flupoxam, flupropacil, flurpyrsulfuron(-methyl, -sodium), flurenol(-butyl), fluridone, fluroxypyr(-meptyl), flurprimidol, flurtamone, fluthiacet(-methyl), fluthiamide, fomesafen, glufosinate(-ammonium), glyphosate-(-isopropylammonium), halosafen, haloxyfop(-ethoxyethyl), haloxyfop(-p-methyl), hexazinone, imazamethabenz-(-methyl), imazamethapyr, imazamox, imazapyr, imazaquin, imazethapyr, imazosulfuron, ioxynil, isopropalin, isoproturon, isouron, isoxaben, isoxaflutole, isoxapyrifop, lactofen, lenacil, linuron, MCPA, MCPP, mefenacet, metarnitron, metazachlor, methabenzthiazuron, metobenzuron, metobromuron, (alpha-)metolachlor, metosulam, metoxuron, metribuzin, metsulfuron(-methyl), molinate, monolinuron, naproanitide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pentoxazone, phenmedipham, piperophos, pretilachlor, primisulfuron(-methyl), prometryn, propachlor, propanil, propaquizafop, propisochlor, propyzamide, prosulfocarb, prosulfuron, pyraflufen(-ethyl), pyrazolate, pyrazosulfuron(-ethyl), pyrazoxyfen, pyribenzoxim, pyributicarb, pyridate, pyrimninobac-(-methyl), pyrithiobac(-sodium), quinchlorac, quinmerac, quinoclamine, quizalofop(-P-ethyl), quizalofop(-P-tefuryl), rimsulfuron, sethoxydim, simazine, simetryn, sulcotrione, sulfentrazone, sulfometuron(-methyl), sulfosate, sulfosulfuron, tebutam, tebuthiuron, terbuthylazine, terbutryn, thenylchlor, thiafluamide, thiazopyr, thidiazimin, thifensulfuron(-methyl), thiobencarb, tiocarbazil, tralkoxydim, triallate, triasulfuron, tribenuron(-methyl), triclopyr, tridiphane, trifluralin and triflusulfuron.

A mixture with other known active compounds, such as fungicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing, scattering.

The active compounds according to the invention can be applied both before and after emergence of the plants. They can also be incorporated into the soil before sowing.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

The preparation and the use of the active compounds according to the invention can be seen from the examples below.

PREPARATION EXAMPLES

Example 1

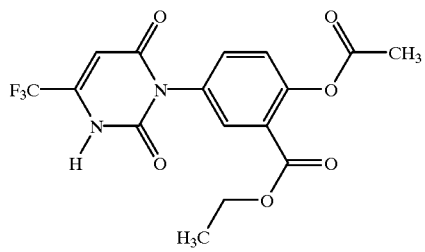

A solution of 13.8 g (40 mmol) of 3-(4-hydroxy-3-ethoxycarbonyl-phenyl)-6-trifluoromethyl-1,2,3,4-tetrahydro-1H-pyrirmidine-2,4-dione in 100 mml of acetic anhydride is heated under reflux for approximately 16 hours. The excess acetic anhydride is distilled off under water pump vacuum, and the residue is stirred twice with 30 ml of diethyl ether each time and dried at 50° C. under reduced pressure.

This gives 11.5 g (74.5% of theory) of 3-(4-acetoxy-3-ethoxycarbonyl-phenyl)-6-trifluoromethyl-1,2,3,4-tetrahydro-1H-pyrimidine-2,4-dione of melting point 155° C.

Example 2

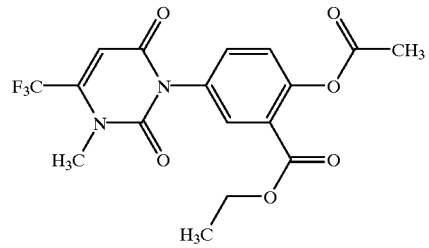

5.0 g (40 mmol) of dimethyl sulphate are added to a mixture of 7.6 g (19.7 mmol) of 3-(4-acetoxy-3-ethoxycarbonyl-phenyl)-6-trifluoromethyl-1,2,3,4-tetrahydro-1H-pyrimidine-2,4-dione and 11.0 g (80 mmol) of potassium carbonate in 50 ml of dimethyl sulphoxide, and the mixture is heated at 50° C. for 5 hours. The reaction mixture is then diluted with water and extracted with dichloromethane. The organic phase is washed successively with saturated aqueous amonium chloride solution and with saturated aqueous sodium chloride solution, dried over magnesium sulphate and freed from the solvent under water pump vacuum. Column-chromatographic separation is carried out on silica gel using dichloromethane/methanol (20:1) as mobile phase.

This gives 6.6 g (84% of theory) of 3-(4-acetoxy-3-ethoxycarbonyl-phenyl)-1-methyl-6-trifluoromethyl-1,2,3,4-tetrahydro-1H-pyrimidine-2,4-dione of melting point 148° C.

Example 3

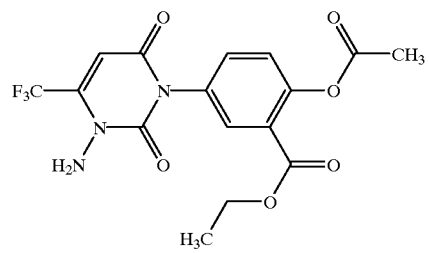

1.0 g (2,9 mmol) of 3-(4-acetoxy-3-ethoxycarbonyl-phenyl)-6-trifluoromethyl-1,2,3,4-tetrahydro-1H-pyrimidine-2,4-dione together with 0.3 g (3.5 mmol) of sodium bicarbonate and 50 ml of N,N-dimethyl-formamide are stirred for one hour. 0.3 g (1.5 mmol) of 1-aminooxy-2,4-dinitro-benzene is then added, and the reaction mixture is stirred at room temperature (approximately 20° C.) for 24 hours. After addition of a further 0.3 g of 1-aminooxy-2,4-dinitro-benzene, the mixture is stirred for a further 24 hours and, after addition of a further 0.15 g of 1-aminooxy-2,4-dinitro-benzene, for a further 48 hours at room temperature. The mixture is then poured into a saturated aqueous sodium chloride solution and extracted repeatedly with ethyl acetate.

The combined organic extracts are washed with water, dried with sodium sulphate and filtered through silica gel. The filtrate is concentrated under water pump vacuum the residue is digested with isopropanol and the crystalline product is isolated by filtration with suction.

This gives 0.7 g (60% of theory) of 1-amino-3-(4-acetoxy-3-ethoxycarbonyl-phenyl)-6-trifluoromethyl-1,2,3,4-tetrahydro-1H-pyrinidine-2,4-dione of melting point 190° C.

Analogously to the Preparation Examples 1 to 3, and in accordance with the general description of the preparation processes according to the invention, it is also possible to prepare, for example, the compounds of the formula (I) listed in Table 1 below.

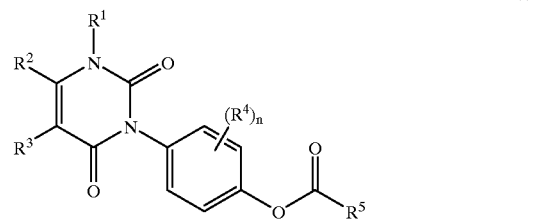

(I)

TABLE 1

Examples of the compounds of the formula (I)

| Ex. No. | n | $R^1$ | $R^2$ | $R^3$ | (position-) $R^4$ | $R^5$ | Physical data |
|---|---|---|---|---|---|---|---|
| 4 | 1 | $CH_3$ | $CF_3$ | Cl | (3-)$COOCH_3$ | $CH_3$ | |
| 5 | 1 | $CH_3$ | $CF_3$ | $CH_3$ | (3-)$COOCH_3$ | $CH_3$ | |
| 6 | 1 | $NH_2$ | $CF_3$ | Cl | (3-)$COOCH_3$ | $CH_3$ | |
| 7 | 1 | $NH_2$ | $CF_3$ | $CH_3$ | (3-)$COOCH_3$ | $CH_3$ | |
| 8 | 1 | $CH_3$ | $CF_3$ | H | (3-)$COOCH_3$ | $C_6H_5$ | |
| 9 | 1 | $CH_3$ | $CF_3$ | $CH_3$ | (3-)$COOCH_3$ | $C_6H_5$ | |
| 10 | 1 | $CH_3$ | $CF_3$ | H | (3-)$COOCH_3$ | 2-thienyl | |
| 11 | 1 | $NH_2$ | $CF_3$ | H | (3-)$COOCH_3$ | 2-thienyl | |
| 12 | 1 | $CH_3$ | $CF_3$ | H | (3-)$COOCH_3$ | $CH(CH_3)_2$ | |
| 13 | 1 | $NH_2$ | $CF_3$ | H | (3-)$COOCH_3$ | $CH(CH_3)_2$ | |
| 14 | 1 | $CH_3$ | $CF_3$ | H | (3-)$COOCH_3$ | cyclopropyl | |
| 15 | 1 | $NH_2$ | $CF_3$ | H | (3-)$COOCH_3$ | cyclopropyl | |
| 16 | 1 | $CH_3$ | $CF_3$ | H | (3-)$COOC_2H_5$ | $CH_2OCH_3$ | |
| 17 | 1 | $NH_2$ | $CF_3$ | H | (3-)$COOC_2H_5$ | $CH_2OCH_3$ | |
| 18 | 1 | $CH_3$ | $CF_3$ | H | (2-)F | 6-chloropyridin-3-yl | |
| 19 | 1 | $CH_3$ | $CF_3$ | H | (2-)Cl | pyridin-3-yl | |
| 20 | 1 | $CH_3$ | $CF_3$ | H | (3-)$CH_3$ | $OC_2H_5$ | |
| 21 | 1 | $CH_3$ | $CF_3$ | H | (3-)$CF_3$ | $SC_6H_5$ | |
| 22 | 1 | $CH_3$ | $CF_3$ | H | (3-)CN | $CH_2C_6H_5$ | |
| 23 | 1 | $CH_3$ | $CF_3$ | H | (3-)$NO_2$ | $CHCl_2$ | |
| 24 | 1 | $CH_3$ | $CF_3$ | H | (3-)$SO_2NH_2$ | $C_2H_5$ | |

TABLE 1-continued

Examples of the compounds of the formula (I)

| Ex. No. | n | $R^1$ | $R^2$ | $R^3$ | (position-) $R^4$ | $R^5$ | Physical data |
|---|---|---|---|---|---|---|---|
| 25 | 1 | $CH_3$ | $CF_3$ | H | (3-)$NHSO_2CH_3$ | 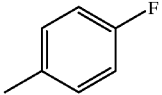 | |
| 26 | 1 | $CH_3$ | $CF_3$ | H | (3-)$CONH_2$ | $CH_3$ | |
| 27 | 1 | $CH_3$ | $CF_3$ | H | (3-)$NHSO_2C_2H_5$ | $CH_3$ | |
| 28 | 1 | $CH_3$ | $CF_3$ | H | (3-)F | $C(CH_3)_3$ | |
| 29 | 1 | $CH_3$ | $CF_3$ | H | (3-)Cl | $CH(CH_3)_2$ | |
| 30 | 1 | $CH_3$ | $CF_3$ | H | (3-)Br | $CH_3$ | |
| 31 | 1 | H | $CF_3$ | H | (3-)$COOC_2H_5$ | $C_6H_5$ | m.p.: 223° C. |
| 32 | 1 | H | $CF_3$ | H | (3-)$COOC_2H_5$ | 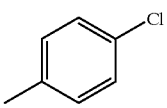 | m.p.: 231° C. |
| 33 | 1 | H | $CF_3$ | H | (3-)$COOC_2H_5$ | 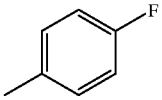 | m.p.: 249° C. |
| 34 | 1 | $CH_3$ | $CF_3$ | H | (3-)$COOC_2H_5$ | $C_6H_5$ | m.p.: 190° C. |
| 35 | 1 | $NH_2$ | $CF_3$ | H | (3-)$COOC_2H_5$ | $C_6H_5$ | m.p.: 170° C. |
| 36 | 1 | H | $CF_3$ | H | (3-)$COOC_2H_5$ | 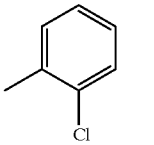 | m.p.: 183° C. |
| 37 | 1 | $CH_3$ | $CF_3$ | H | (3-)$COOC_2H_5$ | 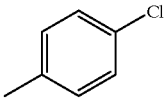 | m.p.: 193° C. |
| 38 | 1 | $CH_3$ | $CF_3$ | H | (3-)$COOC_2H_5$ | 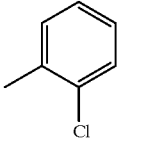 | m.p.: 143° C. |
| 39 | 1 | H | $CF_3$ | H | (3-)$COOC_2H_5$ | 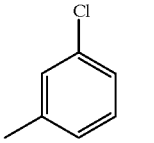 | m.p.: 251° C. |
| 40 | 1 | $CH_3$ | $CF_3$ | H | (3-)$COOC_2H_5$ | 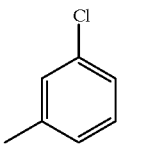 | m.p.: 171° C. |

TABLE 1-continued

Examples of the compounds of the formula (I)

| Ex. No. | n | $R^1$ | $R^2$ | $R^3$ | (position-) $R^4$ | $R^5$ | Physical data |
|---|---|---|---|---|---|---|---|
| 41 | 1 | CH$_3$ | CF$_3$ | H | (3-)COOC$_2$H$_5$ | 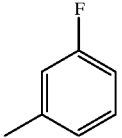 | m.p.: 175° C. |
| 42 | 1 | H | CF$_3$ | H | (3-)NO$_2$ | CH$_3$ | m.p.: 264° C. |
| 43 | 1 | CH$_3$ | CF$_3$ | H | (3-)NO$_2$ | CH$_3$ | m.p.: 185° C. |
| 44 | 1 | H | CF$_3$ | H | (3-)NO$_2$ | C$_2$H$_5$ | m.p.: 222° C. |
| 45 | 1 | CH$_3$ | CF$_3$ | H | (3-)NO$_2$ | C$_2$H$_5$ | m.p.: 187° C. |
| 46 | 1 | CH$_3$ | CF$_3$ | H | 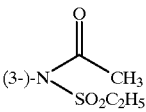 | CH$_3$ | m.p.: 139° C. |
| 47 | 1 | CH$_3$ | CF$_3$ | H | 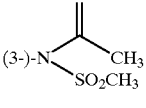 | CH$_3$ | m.p.: 236° C. |
| 48 | 1 | CH$_3$ | CF$_3$ | H | (3-)COOC$_2$H$_5$ | 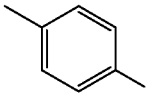 | m.p.: 172° C. |
| 49 | 1 | NH$_2$ | CF$_3$ | H | (3-)COOC$_2$H$_5$ | 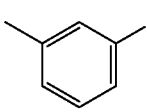 | m.p.: 183° C. |
| 50 | 1 | CH$_3$ | CF$_3$ | H | (3-)COOC$_2$H$_5$ | 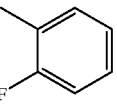 | m.p.: 161° C. |
| 51 | 1 | H | CF$_3$ | H | (3-)COOC$_2$H$_5$ | 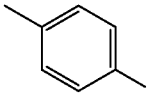 | m.p.: 272° C. |
| 52 | 1 | CH$_3$ | CF$_3$ | H | (3-)COOC$_2$H$_5$ | 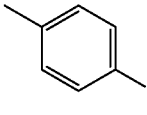 | m.p.: 206° C. |
| 53 | 1 | CH$_3$ | CF$_3$ | H | (3-)COOC$_2$H$_5$ | 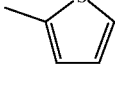 | m.p.: 182° C. |
| 54 | 1 | H | CF$_3$ | H | (3-)COOC$_2$H$_5$ | 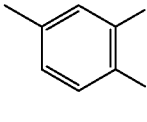 | m.p.: 254° C. |

TABLE 1-continued

Examples of the compounds of the formula (I)

| Ex. No. | n | R¹ | R² | R³ | (position-) R⁴ | R⁵ | Physical data |
|---|---|---|---|---|---|---|---|
| 55 | 1 | H | CF$_3$ | H | (3-)COOC$_2$H$_5$ | 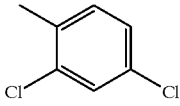 | m.p.: 245° C. |
| 56 | 1 | CH$_3$ | CF$_3$ | H | (3-)COOC$_2$H$_5$ | 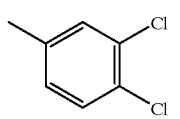 | m.p.: 190° C. |
| 57 | 1 | CH$_3$ | CF$_3$ | H | (3-)COOC$_2$H$_5$ | 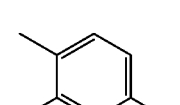 | m.p.: 180° C. |
| 58 | 1 | NH$_2$ | CF$_3$ | H | (3-)COOC$_2$H$_5$ | 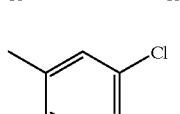 | m.p.: 184° C. |
| 59 | 1 | NH$_2$ | CF$_3$ | H | (3-)COOC$_2$H$_5$ | 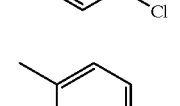 | m.p.: 193° C. |
| 60 | 1 | H | CF$_3$ | H | (3-)COOC$_2$H$_5$ | 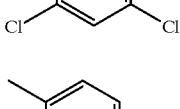 | m.p.: 260° C. |
| 61 | 1 | H | CF$_3$ | H | (3-)COOC$_2$H$_5$ | 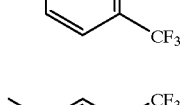 | m.p.: 219° C. |
| 62 | 1 | H | CF$_3$ | H | (3-)COOC$_2$H$_5$ | 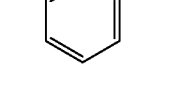 | m.p.: 236° C. |
| 63 | 1 | H | CF$_3$ | H | (3-)COOC$_2$H$_5$ | 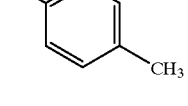 | m.p.: 200° C. |
| 64 | 1 | CH$_3$ | CF$_3$ | H | (3-)COOC$_2$H$_5$ | 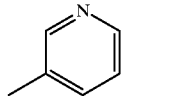 | m.p.: 200° C. |
| 65 | 1 | CH$_3$ | CF$_3$ | H | (3-)COOC$_2$H$_5$ | 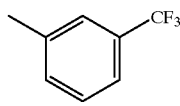 | m.p.: 195° C. |

TABLE 1-continued

Examples of the compounds of the formula (I)

| Ex. No. | n | R¹ | R² | R³ | (position-) R⁴ | R⁵ | Physical data |
|---|---|---|---|---|---|---|---|
| 66 | 1 | CH₃ | CF₃ | H | (3-)COOC₂H₅ | 4-CH₃-C₆H₄ | m.p.: 179° C. |
| 67 | 1 | NH₂ | CF₃ | H | (3-)COOC₂H₅ | 4-Cl-C₆H₄ | m.p.: 182° C. |
| 68 | 1 | CH₃ | CF₃ | H | (3-)COOCH₃ | 4-Cl-C₆H₄ | m.p.: 203° C. |
| 69 | 1 | NH₂ | CF₃ | H | (3-)COOCH₃ | 4-Cl-C₆H₄ | m.p.: 214° C. |
| 70 | 1 | CH₃ | CF₃ | H | (3-)COOCH₃ | 3-Cl-C₆H₄ | m.p.: 175° C. |
| 71 | 1 | CH₃ | CF₃ | H | (3-)COOCH₃ | 2-Cl-C₆H₄ | m.p.: 190° C. |
| 72 | 1 | CH₃ | CF₃ | H | (3-)COOCH₃ | 3-F-C₆H₄ | m.p.: 206° C. |
| 73 | 1 | H | CF₃ | H | (3-)COOC₃H₇-i | 2-Cl-C₆H₄ | m.p.: 235° C. |
| 74 | 1 | H | CF₃ | H | (3-)COOC₃H₇-i | 4-Cl-C₆H₄ | m.p.: 213° C. |
| 75 | 1 | H | CF₃ | H | (3-)COOC₃H₇-i | 3-Cl-C₆H₄ | m.p.: 206° C. |
| 76 | 1 | CH₃ | CF₃ | H | (3-)COOC₃H₇-i | 4-Cl-C₆H₄ | m.p.: 150° C. |
| 77 | 1 | CH₃ | CF₃ | H | (3-)COOC₃H₇-i | 3-Cl-C₆H₄ | m.p.: 164° C. |

TABLE 1-continued

Examples of the compounds of the formula (I)

| Ex. No. | n | R¹ | R² | R³ | (position-) R⁴ | R⁵ | Physical data |
|---|---|---|---|---|---|---|---|
| 78 | 1 | CH₃ | CF₃ | H | (3-)COOC₃H₇-i | 2-chlorophenyl | m.p.: 181° C. |
| 79 | 1 | CH₃ | CF₃ | H | (3-)COOC₃H₇-i | CH₃ | m.p.: 150° C. |
| 80 | 2 | H | CF₃ | H | (3-)COOCH₃/(5-)F | 4-chlorophenyl | (amorphous) |
| 81 | 2 | CH₃ | CF₃ | H | (3-)COOC₂H₅/(5-)F | 4-chlorophenyl | m.p.: 152° C. |
| 82 | 2 | H | CF₃ | H | (3-)COOC₂H₅/(5)-F | 4-chlorophenyl | m.p.: 250° C. |
| 83 | 2 | H | CF₃ | H | (3-)COOCH₃/(5-)F | 2-chlorophenyl | m.p.: 201° C. |
| 84 | 2 | H | CF₃ | H | (3-)COOCH₃/(5-)F | 3-chlorophenyl | m.p.: 180° C. |
| 85 | 1 | NH₂ | CF₃ | H | (3-)COOC₂H₅ | cyclopropyl | m.p.: 158° C. |
| 86 | 2 | H | CF₃ | H | (3-)COOCH₃/(5-)F | CH₃ | m.p.: 210° C. |
| 87 | 2 | CH₃ | CF₃ | H | (3-)COOCH₃/(5-)F | 4-chlorophenyl | m.p.: 173° C. |
| 88 | 2 | CH₃ | CF₃ | H | (3-)COOCH₃/(5-)F | 2-chlorophenyl | m.p.: 134° C. |
| 89 | 2 | CH₃ | CF₃ | H | (3-)COOCH₃/(5-)F | 3-chlorophenyl | m.p.: 152° C. |
| 90 | 2 | CH₃ | CF₃ | H | (3-)COOCH₃/(5-)F | CH₃ | m.p.: 136° C. |
| 91 | 1 | NH₂ | CF₃ | H | (3-)COOC₂H₅ | C₈H₁₇-n | m.p.: 111° C. |
| 92 | 2 | H | CF₃ | H | (3-)COOC₂H₅/(5-)F | 3-chlorophenyl | m.p.: 106° C. |

TABLE 1-continued

Examples of the compounds of the formula (I)

| Ex. No. | n | $R^1$ | $R^2$ | $R^3$ | (position-) $R^4$ | $R^5$ | Physical data |
|---|---|---|---|---|---|---|---|
| 93 | 2 | H | $CF_3$ | H | (3-)$COOC_2H_5$/(5-)F | 2-Cl-phenyl | m.p.: 90° C. |
| 94 | 2 | $CH_3$ | $CF_3$ | H | (3-)$COOC_2H_5$/(5-)F | 3-Cl-phenyl | m.p.: 106° C. |
| 95 | 2 | H | $CF_3$ | H | (3-)$COOCH_3$/(5-)F | 2-F-phenyl | (amorphous) |
| 96 | 2 | $CH_3$ | $CF_3$ | H | (3-)$COOCH_3$/(5-)F | 2-F-phenyl | (amorphous) |
| 97 | 1 | $NH_2$ | $CF_3$ | H | (3-)$COOC_2H_5$ | $C_3H_7$-i | m.p.: 157° C. |
| 98 | 1 | $NH_2$ | $CF_3$ | H | (3-)$COOC_2H_5$ | $C_4H_9$-t | (amorphous) |
| 99 | 2 | H | $CF_3$ | H | (3-)$COOC_2H_5$/(5-)F | $CH_3$ | m.p.: 185° C. |
| 100 | 2 | $CH_3$ | $CF_3$ | H | (3-)$COOC_2H_5$/(5-)F | $CH_3$ | m.p.: 119° C. |
| 101 | 1 | $NH_2$ | $CF_3$ | H | (3-)$COOC_2H_5$ | 4-$C_6H_5$-phenyl | m.p.: 212° C. |
| 102 | 1 | $NH_2$ | $CF_3$ | H | (3-)$COOC_2H_5$ | 2-F-phenyl | m.p.: 190° C. |
| 103 | 2 | $CH_3$ | $CF_3$ | H | (5-)$COOC_2H_5$/(2-)F | 2-F-phenyl | m.p.: 156° C. |
| 104 | 2 | $CH_3$ | $CF_3$ | H | (5-)$COOC_3H_7$-i/(2-)F | 2-F-phenyl | m.p.: 157° C. |

Use Examples

Example A

Pre-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After about 24 hours, the soil is sprayed with the preparation of active compound such that the particular amounts of active compound desired are applied per unit area. The concentration of the spray liquor is chosen so that the particular amounts of active compound desired are applied in 1000 l of water/ha.

After three weeks, the degree of damage to the plants is rated in % damage in comparison with the development of the untreated control.

The figures denote:

0%=no effect (like untreated control)

100%=total destruction

In this test, for example, the compounds of Preparation Example 2 and 3 exhibit very strong action against weeds, and some of them are tolerated well by crop plants, such as, for example, cotton and maize.

Example B

Post-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants having a height of 5–15 cm are sprayed with the preparation of active compound such that the particular amounts of active compound desired are applied per unit area. The concentration of the spray liquor is chosen so that the particular amounts of active compound desired are applied in 1000 l of water/ha.

After three weeks, the degree of damage to the plants is rated in % damage in comparison with the development of the untreated control.

The figures denote:

0%=no effect (like untreated control)

100%=total destruction

In this test, for example, the compounds of Preparation Example 2 and 3 exhibit very strong action against weeds, and some of them are tolerated well by crop plants, such as, for example, oilseed rape and wheat.

What is claimed is:

1. A substituted phenyluracil of the formula (I)

(I)

wherein n represents the numbers 0, 1, 2 or 3,

Q represents oxygen or sulphur, $R^1$ represents hydrogen, represents amino or represents unsubstituted or cyano-, fluorine-, or chlorine-substituted alkyl having 1 to 4 carbon atoms, $R^2$ represents cyano, carboxyl, carbamoyl, thiocarbamoyl or represents in each case unsubstituted or cyano-, fluorine- or chlorine-substituted alkyl or alkylcarbonyl having in each case up to 4 carbon atoms, $R^3$ represents hydrogen, fluorine, chlorine, bromine or alkyl having 1 to 4 carbon atoms, $R^4$ represents nitro, amino, hydroxyl, carboxyl, cyano, carbamoyl, thiocarbamoyl, sulfo, chlorosulphonyl, aminosulphonyl, halogen, or represents in each case unsubstituted or cyano-, halogen- or $C_1$–$C_4$-alkoxy-substituted alkyl, alkoxy, alkylthio, alkylsulphinyl, alkylsulphonyl, alkylamino, alkylcarbonyl, alkoxycarbonyl, alkylaminocarbonyl, alkylcarbonylamino, alkoxycarbonylamino, alkylsulphonylamino, bis-alkylcarbonyl-amino, bis-alkylsulphonyl-amino or N-alkylcarbonyl-N-alkylsulphonyl-amino having in each case up to 5 carbon atoms in the alkyl groups, and $R^5$ represents hydrogen, represents in each case unsubstituted or cyano-, halogen- or $C_1$–$C_4$-alkoxy-substituted alkyl, alkoxy, alkylthio, alkylamino or dialkylamino having in each case 1 to 5 carbon atoms, represents in each case optionally cyano- or halogen-substituted alkenyl, alkenyloxy, alkenylamino, alkinyl, alkinyloxy or alkinylamino having in each case up to 5 carbon atoms, represents in each case unsubstituted or cyano-, halogen- or $C_1$–$C_4$-alkyl-substituted cycloalkyl, cycloalkyloxy, cycloalkylamino, cycloalkylalkyl, cycloalkylalkoxy or cycloalkylalkylamino having in each case 3 to 6 carbon atoms in the cycloalkyl groups and 0 to 3 carbon atoms in the alkyl moieties, represents in each case unsubstituted or nitro-, cyano-, halogen-, $C_1$–$C_4$-alkyl-, $C_1$–$C_4$-halogenoalkyl-, $C_1$–$C_4$-alkoxy-, $C_1$–$C_4$-halogenoalkoxy-, $C_1$–$C_4$-alkylthio-, $C_1$–$C_4$-halogenoalkylthio-, $C_1$–$C_4$-alkylsulphinyl-, $C_1$–$C_4$-halogenoalkylsulphinyl-, $C_1$–$C_4$-alkylsulphonyl-, $C_1$–$C_4$-halogenoalkylsulphonyl- or phenyl-substituted aryl, aryloxy, arylthio, arylamino, arylalkyl, arylalkoxy, arylalkylthio or arylalkylamino having in each case 6 or 10 carbon atoms in the aryl groups and 0 to 3 carbon atoms in the alkyl moieties, or represents in each case unsubstituted or cyano-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted heterocyclyl or heterocyclylalkyl from the group consisting of furyl, tetrahydrofuryl, furyl-$C_1$–$C_4$-alkyl, benzofuryl, benzofuryl-$C_1$–$C_4$-alkyl, thienyl, thienyl-$C_1$–$C_4$-alkyl, benzothienyl, benzothienyl-$C_1$–$C_4$-alkyl, oxazolyl, oxazolyl-$C_1$–$C_4$-alkyl, benzoxazolyl, benzoxazolyl-$C_1$–$C_4$-alkyl, isoxazolyl, isoxazolyl-$C_1$–$C_4$-alkyl, benzisoxazolyl, benzisoxazolyl-$C_1$–$C_4$-alkyl, thiazolyl, thiazolyl-$C_1$–$C_4$-alkyl, benzothiazolyl, benzothiazolyl-$C_1$–$C_4$-alkyl, pyrazolyl, pyrazolyl-$C_1$–$C_4$-alkyl, oxadiazolyl, oxadiazolyl-$C_1$–$C_4$-alkyl, thiadiazolyl, thiadiazolyl-$C_1$–$C_4$-alkyl, pyridyl, pyridyl-$C_1$–$C_4$-alkyl, quinolyl, quinolyl-$C_1$–$C_4$-alkyl, pyrimiyl, pyrimidyl-$C_1$–$C_4$-alkyl.

2. A substituted phenyluracil of the formula (I) according to claim 1, wherein n represents the numbers 0, 1 or 2, Q represents oxygen or sulphur, $R^1$ represents hydrogen, amino, methyl or ethyl, $R^2$ represents cyano, carboxyl, carbamoyl, thiocarbamoyl, methyl, ethyl, fluoromethyl, chloromethyl, difluoromethyl, dichloromethyl, trifluoromethyl, trichloromethyl, chlorodifluoromethyl, fluorodichloromethyl, fluoroethyl, chloroethyl, difluoroethyl, dichloroethyl, chlorofluoroethyl, trifluoroethyl, trichloroethyl, chlorodifluoroethyl, fluorodichloroethyl, pentafluoroethyl, methoxycarbonyl or ethoxycarbonyl, $R^3$ represents hydrogen, chlorine, bromine or methyl, $R^4$ represents nitro, amino, hydroxyl, carboxyl, cyano, carbamoyl, thiocarbamoyl, sulpho, chlorosulphonyl, aminosulphonyl, fluorine, chlorine, bromine, or represents in each case unsubstituted or cyano-, fluorine-, chlorine-, bromine-, methoxy- or ethoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, methylsulphonyl, ethylsulphonyl, methylamino, ethylamino, n- or i-propylamino, n-, i-, s- or t-butylamino, acetyl, propionyl, n- or i-butyroyl, methoxycarbonyl, ethoxycarbonyl, n- or i-propoxycarbonyl, methylaminocarbonyl, ethylaminocarbonyl, acetylamino, propionylamino, n- or i-butyroylamino, methoxycarbonylamino, ethoxycarbonylamino, methylsulphonylamino, ethylsulphonylamino, n- or i-propylsulphonylamino, n-, i-, s- or t-butylsulphonylamino, bis-methylsulphonyl-amino, bis-ethylsulphonyl-amino, N-acetyl-N-methylsulphonyl-amino or N-acetyl-N-ethylsulphonyl-amino, and $R^5$ represents hydrogen, represents in each case unsubstituted or cyano-, fluorine-, chlorine-, methoxy-, ethoxy-, n- or i-propoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino, represents in each case unsubstituted or cyano-, fluorine-, chlorine- or bromine- substituted ethenyl, propenyl, butenyl, propenyloxy, butenyloxy, propenylamino, butenylamino, ethinyl, propinyl, butinyl, propinyloxy, butinyloxy, propinylamino or butinylamino, represents in each case unsubstituted or cyano-, fluorine-, chlorine-, methyl- or ethyl- substituted cyclopropyl, cyclobutyl, cyclopentyl, cyclohexyl, cyclopropyloxy, cyclobutyloxy, cyclopentyloxy, cyclohexyloxy, cyclopropylamino, cyclobutylamino, cyclopentylamino, cyclohexylamino, cyclopropylmethyl, cyclobutylmethyl, cyclopentylmethyl, cyclohexylmethyl, cyclopropylmethoxy, cyclobutylmethoxy, cyclopentylmethoxy, cyclopropylmethylamino, cyclobutylmethylamino, cyclopentylmethylamino or cyclohexylmethylamino, represents in each case unsubstituted or nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy-, trifluoromethoxy-, methylthio-, ethylthio-, difluoromethylthio-, trifluoromethylthio-, methylsulphinyl-, ethylsulphinyl-, trifluoromethylsulphinyl-, methylsulphonyl-, ethylsulphonyl-, trifluoromethylsulphonyl- or phenyl-substituted phenyl, phenoxy, phenylthio, phenylamino, benzyl, benzyloxy, benzylthio or benzylamino, or represents in each case unsubstituted or cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted heterocyclyl or heterocyclylalkyl from the group consisting of furyl, tetrahydrofuryl, furylmethyl, benzofuryl, benzofurylmethyl, thienyl, thienylmethyl, benzothienyl, benzothienylmethyl, oxazolyl, oxazolylmethyl, benzoxazolyl, benzoxazolylmethyl, isoxazolyl, isoxazolylmethyl, benzisoxazolyl, benzisoxazolylmethyl, thiazoyl, thiazolylmethyl, benzothiazolyl, benzothiazolylmethyl, pyrazolyl, pyrazolylmethyl, oxadiazolyl, oxadiazolylmethyl, thiadiazolyl, thiadiazolylmethyl, pyridyl, pyridylmethyl, quinolyl, quinolylmethyl, pyrimidyl, pyrimidyl methyl.

3. An aminouracil of the formula (IIa)

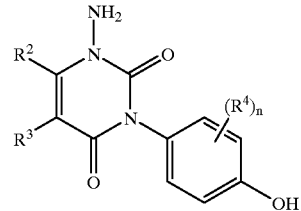

wherein n, $R^2$, $R^3$ and $R^4$ are as defined in claim 1.

4. A process for preparing an aminouracil of the formula (IIa) according to claim 3, comprising the step of reacting a uracil of the formula (IIb)

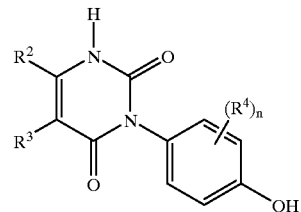

wherein n, $R^2$, $R^3$ and $R^4$ are as defined in claim 1, with an electrophilic aminating agent at a temperature between 0° C. and 100° C.

5. The process of claim 3, wherein the electrophilic aminating agent is 1-aminooxy-2,3-dinitro-benzene.

6. A herbicidal composition, comprising at least one substituted phenyluracil according to claim 1 and one or more extenders and/or surfactants.

7. A method for controlling undesirable plants comprising the step of applying an effective amount of a substituted phenyluracil of the formula (I) according to claim 1, to the undesirable plants and/or their habitat.

8. The process of claim 4 wherein the reaction is carried out in the presence of a diluent and a reaction auxiliary.

9. The process of claim 8, wherein the electrophilic aminating agent is 1-aminooxy-2,3-dinitro-benzene.

10. The process of claim 9, wherein the reaction auxiliary is sodium bicarbonate and the diluent is N,N-dimethylformamide.

* * * * *